United States Patent [19]

Houlihan

[11] 4,228,166

[45] Oct. 14, 1980

[54] 2-KETO-4,5-DIHYDRO-3 (2H)-PYRIDAZINONES, AND THEIR USE IN TREATING MUSCLE TENSION

[75] Inventor: William J. Houlihan, Mountain Lakes, N.J.

[73] Assignee: Sandoz, Inc., East Hanover, N.J.

[21] Appl. No.: 17,353

[22] Filed: Mar. 5, 1979

[51] Int. Cl.² .................... C07D 237/04; A61K 31/50
[52] U.S. Cl. ................................ 424/250; 544/239
[58] Field of Search ........................ 544/239; 424/250

[56] References Cited

U.S. PATENT DOCUMENTS 4,055,644  10/1977  Houlihan .............................. 544/239

*Primary Examiner*—Mark L. Berch
*Attorney, Agent, or Firm*—Gerald D. Sharkin; Robert S. Honor; Thomas O. McGovern

[57] ABSTRACT

Ketone derivatives of 4,5-dihydro-3(2H)-pyridazinones of the formula

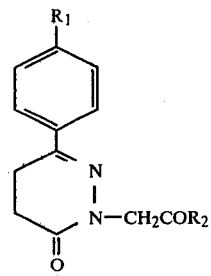

where
$R_1$ is halo having an atomic weight of from 19 to 36, and
$R_2$ is a branched chain lower alkyl having 3 to 4 carbon atoms are useful as central nervous system depressants, in particular, as muscle relaxants.

5 Claims, No Drawings

2-KETO-4,5-DIHYDRO-3 (2H)-PYRIDAZINONES, AND THEIR USE IN TREATING MUSCLE TENSION

This invention relates to ketone derivatives of 4,5-dihydro-3(2H)-pyridazinones. More particularly, it relates to branch chain keto and aryl substituted -4,5-dihydro-3(2H)-pyridazinones, to a method for their preparation and to their use in pharmaceutical compositions.

The compounds of this invention may be represented by the following formula:

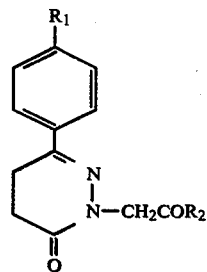

(I)

where
$R_1$ represents halo having an atomic weight of from about 19 to 36, and
$R_2$ represents branched chain lower alkyl of 3 to 4 carbon atoms.

The compound in which $R_1$ is chloro and $R_2$ is isopropyl is especially preferred.

The compounds of formula (I) are prepared in accordance with the following process:

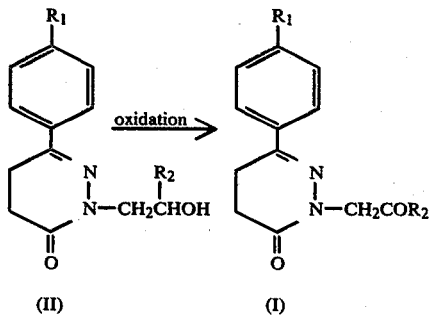

wherein $R_1$ and $R_2$ are as defined above.

The compounds of formula (I) are prepared by oxidizing a compound of formula (II) with an oxidizing agent. The reaction is preferably run in an inert solvent, in particular, water, acetic acid, or mixtures thereof, at temperatures of from about 0° to 40° C., preferably 20° C. for a period of from about 0.5 to 6 hours. The particular solvent, temperature or time at which the reaction is carried out is not critical. The compound of formula (I) is recovered by conventional techniques, e.g., evaporation and recrystallization.

The compounds of formula (II) can be prepared by methods described in U.S. Pat. No. 3,931,176 using known starting materials.

The compounds of formula (I) are useful because they possess pharmacological activity in animals, such as mammals. In particular, the compounds are useful as central nervous system depressants, especially as muscle relaxants, as indicated (1) by their ability to produce docility in behavior tests in mice according to the 30-word adjective check sheet system basically as described by Irwin, S. (Gordon Research Conference, Medicinal Chemistry 1959) and Chen (Symposium on Sedative and Hypnotic Drugs, Williams and Wilkins, 1954) and (2) by the rotored test with trained mice basically as described by Dunham and Miya (J. Am. Pharm. Assoc. 45; 208, 1957).

The compounds of formula (I) may be combined with a pharmaceutically acceptable carrier or adjuvant. They may be administered orally or parenterally. For the above uses, the dosage will vary depending upon the mode of administration utilized and the particular compound employed. However, in general, satisfactory results are obtained when the compounds are administered at a daily dosage of from about 1 milligram to 200 milligrams per kilogram of animal body weight. This daily dosage is preferably given in divided doses, e.g., 2 to 4 times a day, or in sustained release form. For most large mammals, the total daily dosage is from about 75 to 2000 milligrams, and dosage forms suitable for internal administration comprise from about 19 milligrams to about 1000 milligrams of the compound in admixture with a solid or liquid pharmaceutical carrier or diluent.

Tablets and capsules containing the ingredients indicated below may be prepared by conventional techniques and are useful as a muscle relaxant at a dose of one tablet or capsule 2 to 4 times a day.

| Ingredient | Weight tablet | Weight capsule |
|---|---|---|
| 2-(3-methyl-2-oxobutyl)-6-(p-chlorophenyl)-4,5-dihydro-3(2H)-pyridazinone | 100 | 100 |
| tragacanth | 10 | — |
| lactose | 197.5 | 200 |
| corn starch | 25 | |
| talcum | 15 | |
| magnesium stearate | 2.5 | |
| Total | 300 mg. | 300 mg. |

The following pharmaceutical compositions are formulated with the indicated amount of active agent using conventional techniques. The injectable suspension and the oral liquid suspension represent formulations useful as unit doses, which may be administered as muscle relaxants. The injectable suspension is suitable for administration twice a day whereas the oral liquid suspension is suitably administered 2 to 4 times per day for this purpose.

| Ingredient | Weight Injectable | Weight Oral Suspension |
|---|---|---|
| 2-(3-methyl-2-oxobutyl)-6-(p-chlorophenyl)-4,5-dihydro-pyridazin-(2H)-3-one | 100 | 100 |
| sodium carboxy methyl cellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.g. Tween 80) U.S.P. | — | 5 |
| sorbitol solution, 70%, U.S.P. | — | 2,500 |
| buffer agent to adjust pH for | | |

| Ingredient | Weight | |
|---|---|---|
| | Injectable | Oral Suspension |
| desired stability | — | q.s. |
| water | for injection q.s. to 1 ml. | q.s. to 5 ml. |

EXAMPLE 1

2-(3-methyl-2-oxobutyl)-6-(p-chlorophenyl)-4,5-dihydro-3(2H)-pyridazinone

Step 1:
2-(2-hydroxy-3-methylbutyl)-6-(p-chlorophenyl)-4,5-dihydro-3(2H)-pyridazinone A mixture of 9.5 grams (0.085 mol) of 1-hydrazino-3-methyl-2-butanol, 14.4 grams (0.070 mol) of 3-(p-chlorobenzoyl)-propanoic acid and 100 milliliters of toluene are stirred in a flask equipped with a condenser and Dean-Stark water collecting apparatus at reflux for about 2.0 hours during which 2.8 milliliters of water is collected in the Dean-Stark tube. The toluene solution is washed with 50 milliliters of 2 N sodium hydroxide solution, 25 ml. of 2 N hydrochloric acid and then water. The toluene layer is then dried with anhydrous magnesium sulfate, filtered and concentrated in vacuo. The solid obtained is crystallized from methylene chloride-petroleum ether to yield 19.0 grams of 2-(2-hydroxy-3-methylbutyl)-6-(p-chlorophenyl)4,5-dihydropyridazine-3(2H)-one, (m.p. 90°-92° C.)

Step 2:
2-(3-methyl-2-oxobutyl)-6-(p-chlorophenyl)-4,5-dihydro-3(2H)-pyridazinone A solution of 7.0 grams (0.024 mol) of 2-(2-hydroxy-3-methylbutyl)-6-(p-chlorophenyl)-4,5-dihydro-3(2H)-pyridazinone in 2.4 milliliters of acetic acid is cooled with stirring in an icebath, and then over a period of about 5 minutes a solution of 2.2 grams (0.022 mol) of chromium trioxide in 45 milliliters of water is added. The reaction mixture is allowed to stir at room temperature for about 3 hours and then poured onto about 100 milliliters icewater. The mixture is extracted twice with 50 milliliters of methylene chloride and the organic layer is then washed with 30 milliliters of 2 N sodium hydroxide, water, and dried with anhydrous sodium sulfate. After filtration and evaporation to an oil, the product is crystallized from ether to 1.3 grams of 2-(3-methyl-2-oxobutyl)-6-(p-chlorophenyl)-4,5-dihydro-3(2H)-pyridazinone, (m.p. 110°-111° C.)

The $ED_{50}$ of 2-(3-methyl-2-oxobutyl)-6-(p-chlorophenyl)-4,5-dihydro-3(2H)-pyridazinone in the rotorod test, when administered orally to mice, is 167 milligrams per kilogram of animal body weight; and the compound is useful as a muscle relaxant when administered at a dose of 100 milligrams 2 to 4 times a day.

What is claimed is:

1. A method of treating muscle tension in animals which comprises administering to an animal in need of such treatment a therapeutically effective amount of a compound of the formula:

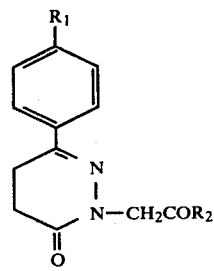

where
$R_1$ is fluoro or chloro and
$R_2$ is branch chain lower alkyl having 3 to 4 carbon atoms.

2. A method according to claim 1 in which 75 to 2000 milligrams of the compound are administered daily.

3. A method according to claim 1 in which 19 to 1000 milligrams of the compound are administered per unit dose.

4. A method according to claim 1 in which 100 milligrams of 2-(3-methyl-2-oxobutyl)-6-(p-chlorophenyl)-4,5-dihydro-3(2H)-pyridazinone is administered 2 to 4 times a day.

5. The method according to claim 1 in which the compound is 2-(3-methyl-2-oxobutyl)-6-(p-chlorophenyl)-4,5-dihydro-3(2H)-pyridazinone.

* * * * *